(12) United States Patent
Welsh et al.

(10) Patent No.: US 6,716,819 B2
(45) Date of Patent: Apr. 6, 2004

(54) USE OF XYLITOL TO REDUCE IONIC STRENGTH AND ACTIVATE ENDOGENOUS ANTIMICROBIALS FOR PREVENTION AND TREATMENT OF INFECTIONS

(75) Inventors: Michael J. Welsh, Riverside, IA (US); Joseph Zabner, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 80 days.

(21) Appl. No.: 09/861,841

(22) Filed: May 21, 2001

(65) Prior Publication Data

US 2002/0022668 A1 Feb. 21, 2002

Related U.S. Application Data

(60) Provisional application No. 60/205,948, filed on May 19, 2000.

(51) Int. Cl.$^7$ ................................................ A61K 31/70
(52) U.S. Cl. ......................................... 514/23; 514/738
(58) Field of Search .................................. 514/23, 738

(56) References Cited

U.S. PATENT DOCUMENTS 5,719,196 A * 2/1998 Uhari et al. ................. 514/738
6,054,143 A * 4/2000 Jones ........................... 424/434

* cited by examiner

*Primary Examiner*—Phyllis G. Spivack
*Assistant Examiner*—C. Delacroix-Muirheid
(74) *Attorney, Agent, or Firm*—McKee, Voorhees & Sease, P.L.C.

(57) ABSTRACT

A method for killing infectious microbial cells by exposing the microbial cells to endogenous antimicrobial compounds. Activation of the antimicrobials is achieved by addition of low permeability, non-ionic osmolytes to lower ionic strength in body fluids where the antimicrobials have been previously suppressed by alteration of ionic transport (increase in salt concentration). The method can be used to treat cystic fibrosis. Cystic fibrosis causes elevated salt concentrations in the airway surface liquid (ASL) occur due to the impaired chloride transport across the epithelia. Xylitol has been found to be an effective low permeability, non-ionic osmolyte for use in the present invention.

16 Claims, 6 Drawing Sheets

USE OF XYLITOL TO REDUCE IONIC STRENGTH AND ACTIVATE ENDOGENOUS ANTIMICROBIALS FOR PREVENTION AND TREATMENT OF INFECTIONS

CROSS-REFERENCE TO RELATED APPLICATIONS

This application claims the benefit of U.S. Provisional Application No. 60/205,948, filed May 19, 2000.

GRANT REFERENCE

This invention was developed with government support under National Institute of Health Contract No. HL 42385, thus the government may have certain rights in this invention.

BACKGROUND OF THE INVENTION

Cystic fibrosis (CF) is a human genetic disease of epithelia. Although the survival rate of those suffering with cystic fibrosis has improved in recent years, the median age for patient survival is still only about 25–30 years despite intensive supportive and prophylactic treatment. Today cystic fibrosis remains the most common congenital disease among Caucasians, where it has a prevalence of about 1 in 2,000 live births and is uniformly fatal. Nearly all patients suffering from the disease develop chronic progressive disease of the respiratory system, the most common cause of death being pulmonary disease. In the majority of cases, pancreatic dysfunction occurs; hepatobiliary and genitourinary disease are also frequent. Because of the multi-system clinical manifestations of the disease, current methods of treatment for the disease have focused on therapeutic approaches to reduce the symptoms of cystic fibrosis.

It is now known that the disease is caused by mutations in the gene encoding the cystic fibrosis transmembrane conductance regulator (CFTR), a phosphorylation-regulated $Cl^-$ channel located in the apical membrane of involved epithelia. Also, much has been discovered about how CF-associated mutations disrupt protein function, thereby disrupting $Cl^-$ transport across CF epithelia.

Despite any advances, the pathogenesis of CF lung disease is still not understood. Lung disease is characterized by bacterial colonization and chronic airway infection. Many organisms can be involved, but *Pseudomonas aeruginosa* and *Staphylococcus aureus* are particularly prominent. Chronic bacterial infections progressively destroy the lung, and may ultimately lead to respiratory failure.

Airway infections currently cause most of the morbidity and mortality in cystic fibrosis (CF) (Taussig, L. M. 1984. Cystic Fibrosis. Georg Thieme Verlag Stuttgart, N.Y.; Davis, P. B. 1993. Pathophysiology of the Lung Disease in Cystic Fibrosis. In Cystic Fibrosis. P. B. Davis, editor. Marcel Dekker, Inc., New York. 193–218; Welsh, M. J., L. -C. Tsui, T. F. Boat and A. L. Beaudet. 1995. Cystic Fibrosis. In The Metabolic and Molecular Basis of Inherited Disease. C. R. Scriver, A. L. Beaudet, W. S. Sly and D. Valle, editors. McGraw-Hill, Inc., New York. 3799–3876; Burns, J. L., B. W. Ramsey, and A. L. Smith. 1993. Clinical manifestations and treatment of pulmonary infections in cystic fibrosis. *Adv. Pediatr. Infect. Dis.* 8:53–56). Infections begin early in the course of disease, are nearly impossible to eradicate, and together with the resulting exuberant inflammation destroy the lung. The pathogenesis of CF airway infection involves a host defense defect that is restricted to the airways; other organs are not infected, and when non-CF lungs are transplanted into a CF patient, they do not become infected (Taussig, L. M. 1984. Cystic Fibrosis. Georg Thieme Verlag Stuttgart, New York; Davis, P. B. 1993. Pathophysiology of the Lung Disease in Cystic Fibrosis. In Cystic Fibrosis. P. B. Davis, editor. Marcel Dekker, Inc., New York. 193–218; Welsh, M. J., L. C. Tsui, T. F. Boat, and A. L. Beaudet. 1995. Cystic Fibrosis. In The Metabolic and Molecular Basis of Inherited Disease. C. R. Scriver, A. L. Beaudet, W. S. Sly and D. Valle, editors. McGraw-Hill, Inc., New York. 3799–3876; Davis, P. B., M. Drumm and M. W. Konstan. 1996, Cystic Fibrosis. *Am. J. Respir. Crit. Care Med.* 154:1229–1256; Wine, J. J. 1999. The genesis of cystic fibrosis lung disease. *J. Clin. Invest.* 103:309–312; Pilewski, J. M., and R. A. Frizzel. 1999. Role of CFTR in Airway Disease. *Physiol Rev.* 79:S215–S255; Quinton, P. 1999. Physiological basis of cystic fibrosis: a historical perspective. *Physiol. Rev.* 79:S3–S22; Accurso, F. J. 1997. Early pulmonary disease in cystic fibrosis. *Curr. Opin. Pulm. Med.* 3:400–403). Early in the disease, many different organisms infect the airways, but with time *Staphylococcus aureus* and *Pseudomonas aeruginosa* predominate (Burns, J. L., J. Emerson, J. R. Stapp, D. L. Yim, J. Krzewinski, L. Louden, B. W. Ramsey and C. R. Clausen. 1998. Microbiology of sputum from patients at cystic fibrosis centers in the United States. *Clin. Infect. Dis.* 27:158–163).

The pathogenesis of CF airway infections and link mutations in the gene encoding the cystic fibrosis transmembrane conductance regulator (CFTR) $Cl^-$ channel to the propensity for infection may be explained as follows (Smith, J. J., S. M. Travis, E. P. Greenberg and M. J. Welsh. 1996. Cystic fibrosis airway epithelia fail to kill bacteria because of abnormal airway surface fluid. *Cell.* 85:229–236; and erratum 287(222)). The thin layer of airway surface liquid (ASL) contains many antimicrobial substances including lysozyme, lactoferrin, secretory leukoproteinase inhibitor (SLPI), human beta defensins 1 and 2, secretory phospholipase A2, and the cathelicidin LL-37 (Arnold, R. R., M. Brewer and J. J. Gauthier. 1980. Bactericidal activity of human lactoferrin: Sensitivity of a variety of microorganisms. *Infect. Immun.* 28:893–898; Jacquot, J., J. M. Tournier, T. G. Carmona, E. Puchelle, J. P. Chazalette and P. Sadoul. 1983. Proteins of bronchial secretions in mucoviscidosis. Role of infection. *Bull. Eur. Physiopathol. Respir.* 19:453–458; Thompson, A. B., T. Bohling, F. Payvandi, and S. I. Rennard. 1990. Lower respiratory tract lactoferrin and lysozyme arise primarily in the airways and are elevated in association with chronic bronchitis. *J. Lab. Clin. Med.* 115:148–158; Hiemstra, P. S., R. J. Maassen, J. Stolk, R. Heinzel-Wieland, G. J. Steffens, and J. H. Dijkman. 1996. Antibacterial activity of antileukoprotease. *Infect. Immun.* 64:4520–4524; Zhao, C., I. Wang, and R. I. Lehrer. 1996. Widespread expression of beta-defensin hBD-1 in human secretory glands and epithelial cells. *FEBS Lett.* 396:319–322; McCray, P. B. and L. Bentley. 1997. Human airway epithelia express a β-defensin. *Am. J. Respir. Cell. Mol. Biol.* 16:343–349; Goldman, M. J., G. M. Anderson, E. D. Stolzenberg, U. P. Kari, M. Zasloff, and J. M. Wilson. 1997. Human β-defensin-1 is a salt-sensitive antibiotic in lung that is inactivated in cystic fibrosis. *Cell.* 88:553–560; Bals, R., X. Wang, Z. Wu, T. Freeman, V. Bafna, M. Zasloff and J. M. Wilson. 1998. Human β-defensin-2 is a salt-sensitive peptide antibiotic expressed in human lung. *J Clin Invest.* 102; Diamond, G., and C. L. Bevins. 1998. Beta-defensins: endogenous antibiotics of the innate host defense response. *Clin. Immunol. Immunopath.* 88:221–225; Bals, R., X. Wang, M. Zasloff and J. M. Wilson. 1998. The peptide antibiotic LL-37/hCAP-18 is expressed in epithelia of the human lung where it has broad antimicrobial activity at the airway surface. *Proc. Nat'l. Acad. Sci. USA.* 95:9541–9546; Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879; Singh, P. K., H. P. Jia, K. Wiles, J. Hesselberth, L. Liu, B. D. Conway, E. Valore, M. J. Welsh, T. Ganz, B. F. Tack and P. B. J. McCray. 1998. Constitutive and inducible expression of β-defensin antimicrobial peptides by human airway epithelia. Unpublished.). These agents acting alone and synergistically form part of the local pulmonary host defense system, killing the small numbers of bacteria that are constantly being deposited on the airway surface. Importantly, an increase in salt concentration inhibits the antibacterial activity of nearly all these agents and attenuates synergy between agents (Goldman, M. J., G. M. Anderson, E. D. Stolzenberg, U. P. Kari, M. Zasloff, and J. M. Wilson. 1997. Human β-defensin-1 is a salt-sensitive antibiotic in lung that is inactivated in cystic fibrosis. *Cell.* 88:553–560; Bals, R., X. Wang, Z.Wu, T. Freeman, V. Bafna, M. Zasloff and J. M. Wilson. 1998. Human β-defensin-2 is a salt-sensitive peptide antibiotic expressed in human lung. *J. Clin. Invest.* 102; Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879; Singh, P. K., H. P. Jia, K. Wiles, J. Hesselberth, L. Liu, B. D. Conway, E. Valore, M. J. Welsh, T. Ganz, B. F. Tack, and P. B. J. McCray. 1998. Constitutive and inducible expression of β-defensin antimicrobial peptides by human airway epithelia. Unpublished; Davies, R. C., A. Neuberger. and B. M. Wilson. 1969. The dependence of lysozyme on pH and ionic strength. *Biochim. Biophys. Acta.* 178:294–305; Millar, M. 1987. The susceptibility to lysozyme of b-lactamase-producing and non-producing derivatives of *Staphylococcus aureus* strain 1030. *J. Med. Microbiol.* 23:127–132; Valore, E. V., C. H. Park, A. J. Quayle, K. R. Wiles, P. B. J. McCray, and T. Ganz. 1998. Human β-defensin-1: An antimicrobial peptide of urogenital tissues. *J. Clin. Invest.* 101:1633–1642; Singh, P., and M. J. Welsh. 1999. Components of airway surface fluid have synergistic antimicrobial activity. *Pediatr. Pulmonol.* Suppl 14:323). In CF, the loss of the CFTR Cl⁻ channel leads to a higher ASL salt concentration which reduces antimicrobial potency, thereby impairing the innate immune system and predisposing to infection.

Evidence for an elevated salt concentration in CF ASL came from in vivo studies that collected tiny volumes (<1 μl) of ASL from trachea and bronchus of anesthetized subjects (Joris, L., I. Dab, and P. M. Quinton. 1993. Elemental composition of human airway surface fluid in healthy and diseased airways. *Am. Rev. Respir. Dis.* 148:1633–1637). Using an in vitro model of differentiated human airway epithelia and a non-invasive isotope method, at equilibrium, non-CF ASL was found to have $Na^+$ and $Cl^-$ concentrations of ~40–50 mM, whereas CF values were ~85–95 mM (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). In contrast, in vivo studies using filter paper to collect ~20 μl of liquid from bronchus (Knowles, M. R., J. M. Robinson, R. E. Wood, C. A. Pue, W. M. Mentz, G. C. Wager, J. T. Gatzy, and R. C. Boucher. 1997. Ion composition of airway surface liquid of patients with cystic fibrosis as compared with normal and disease-control subjects. *J. Clin. Invest.* 100:2588–2595; Hull, J., W. Skinner, C. Robertson, and P. Phelan. 1998. Elemental content of airway surface liquid from infants with cystic fibrosis. *Am. J. Respir. Crit. Care Med.* 157:10–14) led to the conclusion that ASL had NaCl concentrations equal to that of serum, and that there was no difference between CF and non-CF. A potential explanation for the difference between the studies is that the filter paper sampling technique may have altered ASL composition. Earlier studies showed that filter paper draws liquid from the serum; thus the more liquid collected, the more the contamination with serum (Erjefält, I., and C. G. A. Persson. 1990. On the use of absorbing discs to sample mucosal surface liquids. *Clin. Exp. All.* 20:193–197). Additional studies done at equilibrium with in vitro models of human airway epithelia grown at the air-liquid interface (Widdicombe, J. H., H. Fischer, C. Y. -C. Lee, S. N. Uyekubo, and S. S. Miller. 1997. Elemental composition of airway surface liquid. *Pediatric Pulmonology. Suppl.* 14:74; Jacquot, J., O. Tabary, S. Baconnais, G. Balossier, D. Hubert, J. Couetil, and E. Puchelle. 1998. Highly increased levels of constitutive sodium chloride and C-X-C chemokines production by CF human bronchial submucosal gland cells. *Pediatric Pulmonology.* Suppl. 17:387) and xenografts of human airway epithelia (Goldman, M. J., G. M. Anderson, E. D. Stolzenberg, U. P. Kari, M. Zasloff, and J. M. Wilson. 1997. Human β-defensin-1 is a salt-sensitive antibiotic in lung that is inactivated in cystic fibrosis. *Cell.* 88:553–560; Zhang, Y., and J. F. Engelhardt. 1999. Airway surface fluid volume and Cl content in cystic fibrosis and normal bronchial xenografts. *Am. J. Physiol.* 276:469–476; Baconnais, S., R. Tirouvanziam, J. M. Zahm, S. de Bentzmann, B. Peault, G. Balossier, and E. Puchelle. 1999. Ion composition and rheology of airway liquid from cystic fibrosis fetal tracheal xenografts. *Am. J. Respir. Cell. Mol. Biol.* 20:605–611) indicate that the non-CF ASL NaCl concentration is much lower than that of serum, and that ASL salt concentrations are higher in CF. Consistent with this data, in vitro and in vivo studies in rodents indicate that the ASL NaCl concentration is much lower than that of serum (Cowley, E. A., K. Govindaraju, D. K. Lloyd, and D. H. Eidelman. 1997. Is mouse airway surface fluid hypotonic. *Pediatric Pulmonology. Suppl.* 14:233; Cowley. E. A., K. Govindaraju, D. K. Lloyd, and D. H. Eidelman. 1997. Airway surface fluid composition in the rat determined by capillary electrophoresis. *American Physiological Society.* 273:L895–L899; Bacconais, S., J. Zahm, L. Kilian, P. Bonhomme, D. Gobillard, A. Perchet, E. Puchelle, and G. Balossier. 1998. X-ray microanalysis of native airway surface liquid collected by cryotechnique. *J. Microsc.* 191:311–319; McCray, P. B. J., J. Zabner, H. P. Jia, M. J. Welsh, and P. S. Thorne. 1999. Efficient killing of inhaled bacteria in ΔF508 mice: role of airway surface composition. *Am. J. Physiol.* 277:L183–L190).

Based on the salt sensitivity of endogenous antimicrobials and the elevated salt content in CF ASL, it was studied whether lowering the ASL NaCl concentration could help prevent CF airway infections. Several factors were considered. First, the airway epithelium is water permeable (Folkesson, H. G., M. A. Matthay, A. Frigeri and A. S. Verkman. 1996. Transepithelial water permeability in microperfused distal airways. *J. Clin. Invest.* 97:664–671). Consistent with this, when large volumes of liquid are placed on the apical surface, liquid absorption is isotonic (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403; Matsui, H., B. R. Grubb, R. Tarran, S. H. Randell, J. T. Gatzy, C. W. Davis, and R. C Boucher.

1998. Evidence for periciliary liquid layer depletion, not abnormal ion composition, in the pathogenesis of cystic fibrosis airways disease. *Cell.* 95:1005–1015). Thus, if water were simply added to the airway surface, electrolyte concentrations would rapidly return to equilibrium values. However, if an osmolyte that has a low transepithelial permeability were added to the ASL, it might serve to lower the salt concentration. Somewhat analogous to this, the relatively impermeable osmolyte lactose allows the water-permeable mammary gland duct epithelium to maintain the lumenal NaCl concentration at 5–10 mM (Neville, M. C., P. Zhang, and J. C. Allen. 1995. Minerals, ions and trace elements in milk. In Handbook of Milk Composition. Academic Press. 577–675). Second, an osmolyte that is non-ionic would be required, because it is ionic strength which inhibits antimicrobial activity, not osmolarity (Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879; Neville, M. C., P. Zhang, and J. C. Allen. 1995. Minerals, ions and trace elements in milk. In Handbook of Milk Composition. Academic Press. 577–675). Third, the osmolyte should not provide a ready carbon source for bacterial growth. Fourth, the osmolyte should be safe in humans. Fifth, because many endogenous antimicrobials kill very quickly (Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879), even a transient decrease in ionic strength might be effective. Finally, a small reduction in the salt concentration, perhaps only 10 mM, might be beneficial because there is no unique relationship between antimicrobial activity and ionic strength; the lower the ionic strength, the greater the bacterial killing (Goldman, M. J., G. M. Anderson, E. D. Stolzenberg, U. P. Kari, M. Zasloff, and J. M. Wilson. 1997. Human β-defensin-1 is a salt-sensitive antibiotic in lung that is inactivated in cystic fibrosis. *Cell.* 88:553–560; Bals, R., X. Wang, Z. Wu, T. Freeman, V. Bafna, M. Zasloff, and J. M. Wilson. 1998. Human β-defensin-2 is a salt-sensitive peptide antibiotic expressed in human lung. *J. Clin. Invest.* 102; Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879; Singh, P. K., H. P. Jia, K. Wiles, J. Hesselberth, L. Liu, B. D. Conway, E. Valore, M. J. Welsh, T. Ganz, B. F. Tack, and P. B. J. McCray. 1998. Constitutive and inducible expression of β-defensin antimicrobial peptides by human airway epithelia. Unpublished).

Current methods to treat CF infections are only partially effective and are not directed at the underlying defect. As can be seen from the foregoing, there is a need for a method of treating these infections which addresses the underlying defect. Furthermore, there is a general need for a method of preventing and/or treating epithelial infections.

SUMMARY OF THE INVENTION

An object of the invention is to provide a method for lowering ionic strength in body fluids.

Another object of the invention is to provide a method for killing infectious microbial cells by lowering the ionic strength of bodily fluids in which endogenous antimicrobials are found.

A further object of the invention is a method to lower ionic strength of body fluids by addition of a non-permeable, non-ionic osmolyte, such as xylitol.

An additional object of the invention is a method to prevent and/or treat epithelial infections.

These and other objects, features, and advantages will become apparent after review of the following description and claims of the invention which follow.

The present invention uses application of low permeability, non-ionic osmolyte(s) to allow endogenous antimicrobials to kill infectious microbial cells by decreasing ionic strength in fluids where the endogenous antimicrobials are found.

In CF, the low permeability osmolyte(s) are applied to the apical surface of CF airway epithelia to reduce the salt concentration in the surface liquid. The low permeability osmolytes allow CF epithelia to maintain and increase a transepithelial NaCl concentration gradient.

The preferred non-absorbable osmolyte is xylitol, a 5-carbon polyol. Xylitol has a low transepithelial permeability, is poorly metabolized by bacteria, and can lower the ASL salt concentration in both CF and non-CF airway epithelia in vitro.

When bacteria were deposited into xylitol-containing liquid covering CF epithelia, the bacteria were killed. In contrast, bacteria grew when they were deposited on untreated airway epithelia or epithelia treated with a saline solution. Xylitol is not an antibiotic on its own, instead it allows the killing of bacteria simply because it lowers the NaCl concentration of the surface liquid, thereby enhancing the activity of the endogenous antimicrobials.

BRIEF DESCRIPTION OF THE DRAWINGS

FIGS. 1(A–C). Permeability of xylitol added to the apical surface of non-CF epithelia. Xylitol (138 mM in 60 μl) was added to the apical surface of differentiated airway epithelia at time zero. Apical liquid was removed and volume determined at times indicated. Xylitol was measured by NMR. Data are mean±SEM; n=4. Some SEM bars are hidden by symbols.

FIG. 2. Effect of apical xylitol on rate of liquid absorption by non-CF and CF epithelia. Sixty μl of saline solution, xylitol solution, or indicated mixtures of the two were applied to the apical surface. Four hours later the solution was removed to measure rate of liquid absorption. A short incubation period was chosen to avoid secondary changes in the epithelium due to the large volume of apical liquid. Data are mean±SEM; n=15 from 3 different experiments. Some SEM bars are hidden by symbols.

FIGS. 3(A–B). The effect of apical xylitol on non-CF and CF ASL Cl$^-$ concentration and volume. Five μl of isosmotic xylitol or saline solution were applied to the apical surface. Twenty-four hours later, ASL Cl$^-$ concentration (A) and volume (B) were determined. Asterisk indicates a difference between the saline and the xylitol solutions, p<0.05. N=15 to 18 from 3 CF and 3 non-CF specimens.

FIGS. 5(A–G). Effect of xylitol on growth of different airway pathogens. A, B and C. Growth of *P. aeruginosa* (A), *S. aureus*, (B), and coagulase-negative Staphylococcus (C) were measured as O. D. M9 media alone is indicated by open triangle. Xylitol (closed circle), or succinate, mannitol, or sucrose (open circles), were added to M9 media at 100 mM as indicated. D. Nasal swabs were collected and cultured for 3 days in Lauria-Bertani media (open circles), in minimal M9 media (open squares), or in M9 media supplemented with 100 mM xylitol (closed circles). E, F and G. *P. aeruginosa* (E), *S. aureus* (F), and coagulase-negative Staphylococcus (G) were cultured in Lauria-Bertani media alone (open triangles), Lauria-Bertani media with 100 mM xylitol (closed circles), and Lauria-Bertani media containing tobramycin or levofloxacin (open circles).

DETAILED DESCRIPTION OF THE INVENTION

Airway infections are a major cause of morbidity and 95% of the mortality in cystic fibrosis. Current methods to treat CF infections are only partially effective and current treatments are not directed at the underlying defect. The thin layer of liquid covering normal epithelia contains antimicrobial peptides that kill bacteria. Airway surface liquid covering CF epithelia also contains antimicrobial peptides, but their activity is impaired because the loss of CFTR Cl⁻ channels increases the salt concentration of surface liquid.

The present invention uses application of low permeability, non-ionic osmolyte(s) to decrease the ionic strength of fluids containing endogenous antimicrobials in order to increase the activity of these antimicrobials. The decrease in salt concentration also relieves attenuation of the synergy between these endogenous antimicrobials due to increased salt concentration.

For example, by lowering the ASL ionic strength and enhancing the effectiveness of endogenous antimicrobials, xylitol administration to the airway surface is of value in preventing or delaying the onset of CF respiratory tract infections. In treatment of CF, the application of low permeability, non-ionic osmolyte(s) is to the apical surface of CF airway epithelia to reduce the salt concentration in the surface liquid. An osmolyte with a low transepithelial permeability lowers the ASL salt concentration and enhances innate immunity by activating endogenous antimicrobials. Low permeability osmolytes, such as xylitol, a 5-carbon polyol, allow CF epithelia to maintain and increase a transepithelial NaCl concentration gradient. When bacteria were deposited into xylitol-containing liquid covering CF epithelia, the bacteria were killed. In contrast, bacteria grew when they were deposited on untreated airway epithelia or epithelia treated with a saline solution. Xylitol is not an antibiotic on its own, instead it allows the killing of bacteria simply because it lowers the NaCl concentration of the airway surface liquid (ASL)(lowers the ionic strength of ASL), thereby enhancing the activity of the endogenous antimicrobials. Enhancing the activity of endogenous ASL antibacterial factors could have significant advantages for prevention. These factors have broad-spectrum activity against gram positive and gram negative bacteria, including the organisms that are major CF pathogens (Arnold, R. R., M. Brewer and J. J. Gauthier. 1980. Bactericidal activity of human lactoferrin: Sensitivity of a variety of microorganisms. *Infect. Inmun.* 28:893–898; Jacquot, J., J. M. Tournier, T. G. Carmona, E. Puchelle, J. P. Chazalette and P. Sadoul. 1983. Proteins of bronchial secretions in mucoviscidosis. Role of infection. *Bull. Eur. Physiopathol. Respir.* 19:453–458; Thompson, A. B., T. Bohling, F. Payvandi and S. I. Rennard. 1990. Lower respiratory tract lactoferrin and lysozyme arise primarily in the airways and are elevated in association with chronic bronchitis. *J. Lab. Clin. Med.* 115:148–158; Hiemstra, P. S., R. J. Maassen, J. Stolk, R. Heinzel-Wieland, G. J. Steffens and J. H. Dijkman. 1996. Antibacterial activity of antileukoprotease. *Infect. Immun.* 64:4520–4524; Zhao, C., I. Wang and R. I. Lehrer. 1996. Widespread expression of beta-definsin hBD-1 in human secretory glands and epithelial cells. *FEBS Lett.* 396:319–322; McCray, P. B. and Bentley. 1997. Human airway epithelia express a β-defensin. *Am. J. Rspir. Cell. Mol. Biol.* 16:343–349; Goldman, M. J., G. M. Anderson, E. D. Stolzenberg, U. P. Kari, M. Zasloff, and J. M. Wilson. 1997. Human β-defensin-1 is a salt-sensitive antibiotic in lung that is inactivated in cystic fibrosis. *Cell.* 88:553–560; Bals, R., X. Wang, Z. Wu, T. Freeman, V. Bafna, M. Zasloff and J. M. Wilson. 1998. Human β-defensin-1 is a salt-sensitive peptide antibiotic expressed in human lung. *J Clin Invest.* 102; Diamond, G. and C. L. Bevins. 1998. Beta-defensins: endogenous antibiotics of the innate host defense response. *Clin. Immunol. Immunopath.* 88:221–225; Travis, S. M., B. A. D. Conway, J. Zabner, J. J. Smith, N. N. Anderson, P. K. Singh, E. P. Greenberg and M. J. Welsh. 1999. Activity of Abundant Antimicrobials of the Human Airway. *Am. J. Respir. Cell Mol. Biol.* 20:872–879; Singh, P. K., H. P. Jia, K. Wiles, J. Hesselberth, L. Liu, B. D. Conway, E. Valore, M. J. Welsh, T. Ganz, B. F. Tack and P. B. J. McCray. 1998. Constitutive and inducible expression of β-defensin antimicrobial peptides by human airway epithelia. Unpublished; Watanabe, S. K. Matsushita, P. G. J. McCray and J. B. Stokes. 1998. Developmental expression of the epithelial Na channel (ENaC) in rat kidney and uroepithelium. *FASEB J.* 12:A983). Perhaps of greatest significance, most bacteria, even the major CF pathogens, do not show resistance to antibacterial peptides despite growth in the presence of sub-inhibitory concentrations (Fujii, C. A., A. F. Boggs, M. A. Hurst and D. A. Mosca. 1999. In vitro antimicrobial activity of the protegrin analog IB-367 against cystic fibrosis relevant bacterial pathogens. *Pediatr. Pulmonol. Suppl.* 19:319). In striking contrast, when currently available pharmaceutical antibiotics are administered to prevent or treat CF infections, resistance rapidly emerges (Welsh, M. J. L. C. Tsui, T. F. Boat and A. L. Beaudet. 1995. Cystic Fibrosis. In The Metabolic and Molecular Basis of Inherited Disease. C. R. Scriver, A. L. Beaudet, W. S. Sly and D. Valle, editors. McGraw-Hill, Inc., New York. 3799–3876). *P. aeruginosa* is particularly notorious in this regard. Although in vitro acquired resistance to lysozyme has been reported (Fleming, A. 1929. A bacteriolytic ferment found normally in tissues and secretions. *The Lancet:*217–220), it seems likely that resistance to the mixture of endogenous factors will be uncommon given the long period of coevolution of humans and bacteria. Thus, enhancing the activity endogenous antibacterial factors might prove an effective preventive strategy.

Although xylitol might be of value in preventing airway infections for several reasons it appears unlikely that enhancing the activity of endogenous antimicrobials would sufficiently treat infections once established. First, when chronic airway infections develop, they often exist as biofilms that are extremely resistant to antibiotics (Buckholz, R. G. and M. A. Gleeson. 1991. Yeast systems for the commercial product of heterologous proteins. *Biotechnology (NY)* 9:1067–1072), including endogenous antimicrobial factors (Singh, P. K., M. R. Parsek, J. W. Costerton, E. P. Greenberg and M. J. Welsh. 1999. *Pseudomonas aeruginosa* biofilms are resistant to killing by airway surface liquid antimicrobial factors. *Pediatr. Pulmonol.* Suppl. 19:322).

Second, endogenous antimicrobial factors are more important in the innate immune defense to small numbers of bacteria; once infections develop, phagocytes and the acquired immune system become more important. Third, there is a significant inoculum effect, such that with large numbers of bacteria the potency of endogenous antimicrobial factors is reduced (Smith, J. J., S. M. Travis, E. P. Greenberg and M. J. Welsh. 1996. Cystic fibrosis airway epithelia fail to kill bacteria because of abnormal airway surface fluid. *Cell.* 85:229–236; and erratum 287(222); Thrupp, L. D. 1986. Susceptibility testing of antibiotics in liquid media. In antibiotics in Laboratory Medicine. V. Lorian, editor. Williams & Wilkins, Baltimore. 93; and Unpublished). Fourth, in established infections, it is possible that bacterial might develop the ability to metabolize xylitol (Doten, R. C. and R. P. Mortlock. 1985. Characterization of xylitol-utilizing mutants of *Erwinia uredovora. J. Bacteriol.* 161:529–533; Söderling, E., L. Trahan and M. Lenander-Lumikari. 1998. Growth of xylitol-resistant versus xylitol-sensitive Streptococcus mutans strains in saliva. *Acta Odontol Scand.* 56:116–121). However, it is not known whether growth of *P. aeruginosa* or other organisms is limited by lack of metabolic substrate. Finally, once established, infection and inflammation alter the airway architecture causing chronic bronchiectasis, a difficult therapeutic challenge even in patients who do not have CF.

ASL contains numerous antimicrobial peptides and proteins, including lysozyme, lactoferrin, secretory leukoproteinase inhibitor (SLPI), human beta defensins 1 and 2, secretory phospholipase A2, and the cathelicidin LL-37. The activity of all of these is increased at a reduced ionic strength. There is no absolute concentration of salt that inhibits the activity of endogenous antimicrobials. The increase in activity of the endogenous antimicrobials is due to a decrease in ionic strength as opposed to any changes in osmolarity. There is no unique relationship between antimicrobial activity and ionic strength; the lower the ionic strength, the greater the bacterial killing. Since it is believed that any decrease in ionic strength of the fluid will produce the desired effect and that even a transient decrease will be effective to increase antimicrobial action, there is no threshold application level of the osmolyte. The antibacterial activity of endogenous antimicrobials is quite fast (minutes) compared to pharmaceutical antibiotics. Thus, even a transient reduction in ASL ionic strength may be effective. The synergistic activity of endogenous antimicrobials is also markedly enhanced at low ionic strength. Bacteria have little if any ability to develop resistance to single endogenous antimicrobials; it is extremely unlikely that they could develop resistance to the multiple antimicrobials in ASL. Individual airway antimicrobial peptides and proteins show broad spectrum activity against gram positive and gram negative bacteria, some yeast, and some enveloped viruses. In combination, airway antimicrobials will have a very broad spectrum of activity.

Xylitol is not the only agent that can be used; studies demonstrate that other non-ionic osmolytes affecting low transepithelial permeability might be effective. It is believed that any low permeability, non-ionic osmolyte, or mixture of low permeability, non-ionic osmolytes, will be effective. The osmolyte should not provide a ready carbon source for bacterial growth and be safe in humans. Though xylitol has been shown to be effective, one of ordinary skill in the art will be able to determine other substances which will be effective.

In the current invention, xylitol could be administered as a powder or as an aerosol. One of skill in the art would be able to determine other formulations or methods of administration which would be effective.

Dosage of xylitol, or other non-absorbable, non-ionic osmolyte, can be readily determined by one of skill in the art. For example, dosage for the airway can be estimated as follows:

The airways from the trachea to the respiratory bronchioles have an estimated surface area of 1400 $cm^2$ (Weibel, E. R., 1963 Morphometry of the human lung. Berlin: Springer Verlag).

An estimate of ASL depth is 10–20 $\mu$m.

Thus, total volume of ASL is 1.4–2.8 ml.

If the goal is to deliver 1.4 to 2.8 ml of a 300 mM solution, this would be expected to reduce ASL NaCl concentration by half immediately and then further as active ion transport pulled NaCl out of the ASL.

For 1.4 ml the dose can be calculated as 1.4 ml×152.15 g/L×0.3×(1 L/1000 ml)=64 mg.

For 2.8 ml, the calculated dose is 128 mg.

If xylitol were delivered as a powder, it is likely that less could be delivered. The dose of xylitol could be altered to increase the effect on ionic strength.

Xylitol, a 5-carbon sugar, is poorly metabolized by any bacteria (1984. Gram-negative aerobic rods and cocci. In Bergey's Manual of Systemiatic Bacteriology. Vol. 1. J. G. Holt, editor. Lippincott, Williams and Wilkins). Xylitol is nontoxic and is widely used as a bulk sweetener. Interestingly, when incorporated in chewing gum, xylitol is reported to prevent dental caries (Edgar, W. M. 1998. The benefits of using sugar-free chewing gum: a proven anti-caries effect. *Br. Dent J.* 184:29–32; Hujoel, P. P., K. K. M äkinen, C. A. Bennett, K. P. Isotupa, P. J. Isokangas, P. Allen, and P. -L. Mäkinen. 1999. The optimum time to initiate habitual xylitol gum-chewing for obtaining long-term caries prevention. *J. Den. Res.* 78:797–803). Moreover, in chewing gum, lozenges, or syrup, xylitol decreases the incidence of acute otitis media by 20–40% (Uhari, M., T. Kontiokari, M. Koskela, M. Niemelä, and J. Luotonen. 1996. Xylitol chewing gum in prevention of acute otitis media: double blind randomised trial. *Br. Med. J.* 313:1180–1183; Uhari, M., T. Kontiokari, and M. Niemelä. 1998. A novel use of xylitol sugar in preventing acute otitis media. *Pediatrics.* 102:879–884). Therefore, xylitol applied to the apical surface of human airway epithelia was tested for lowering ASL salt concentration in both CF and non-CF airway epithelia. The effect of xylitol on bacteria in vitro and in vivo was also examined. Because airway epithelium is relatively impermeable to xylitol, it may be able to maintain a low ionic strength for a prolonged period of time.

An advantage to the present invention is there will not be immune responses to xylitol, or similar low permeability, non-ionic osmolyte. This is not the case with conventional pharmaceutical antibiotics. Another advantage is that because xylitol can be delivered as an isosmotic solution, it would not be irritating, cause cough, or bronchoconstriction.

Although none of the subjects tested reported adverse effects of xylitol or saline, safety has not been rigorously tested. As with any addition to the body, there are potential drawbacks to treatment with xylitol if given in sufficiently large quantities. Nevertheless, xylitol should be relatively non-toxic; it is present in many foods, and it has been administered intravenously in large doses to humans (Spitz, I. M., A. H. Rubenstein, I. Bersohn and K. H. Bassler. 1970. Metabolism of xylitol in health subjects and patients with renal disease. *Metabolism.* 19:24). xylitol can cause osmotic diarrhea in children when delivered in large amounts. Xylitol has been delivered intravenously as a 5–50% solution in water at 1–4.5 g/Kg as a source of calories. Toxicity has been observed including increases in serum uric acid and elevated liver enzymes. These changes were reversible and may have been due in large part to hyperosmolar effects of the solution. In addition, other agents, including hypertonic mannitol and hypertonic saline solutions have been safety aerosolized to patients with bronchiectasis and CF to improve cough and sputum clearance (Robinson, M., J. A. Regnis, D. L. Bailey, M. King, G. Bautovich and P. T. P. Bye. 1996. Effect of hypertonic saline, amiloride and cough on mucociliary clearance in patience with cystic fibrosis. *Am. J. Respir. Crit. Care Med.* 153:1503–1509; Daviskas, E., S. D. Anderson, S. Eberl, H. K. Chan and G. Bautovich. 1999. Inhalation of dry powder mannitol improves clearance of mucus in patents with bronchiectasis. *Am. J. Respir. Crit. Care Med.* 159:1843–1848; Robinson, M., E. Daviskas, S. Eberl, J. Baker, H. K. Chan, S. D. Anderson and P. T. Bye. 1999. The effect of inhaled mannitol on bronchial mucus clearance in cystic fibrosis patients: a pilot study. *Eur. Respir. J.* 14:678–685).

Though the present invention has been shown to be effective in CF epithelia for prevention of infections, it is believed that the invention will also be effective with other infections and other areas of epithelia. Endogenous antimicrobials are active against some bacteria and enveloped viruses. Therefore, a reduction of ionic strength with xylitol (or other low permeability non-ionic osmolyte) is expected to be of value in preventing or treating infections by any of the infectious microbes for which there are endogenous antimicrobials. The present method could be used for treatment or prevention of respiratory infections. The invention could be used for ventilator-dependent pneumonia, chronic bronchitis, and others. Prevention of ventilator-associated pneumonia would be very valuable since this disease has high mortality and attempts to prevent it with current pharmaceutical antibiotics have led to rapid development of resistant organisms. (Kollef, M. H. 1999. The prevention of ventilator-associated pneumonia. *New Eng. J. Med.* 630:627–634). Xylitol might be used to decrease the ionic strength of liquid bathing other epithelial surfaces and thereby increase the activity of endogenous antimicrobials. In addition to the respiratory tract, other body parts or surfaces which have body fluids containing antimicrobials include the external eye which is bathed with abundant antimicrobials, the pharynx, and the vagina.

It is also believed that the present invention can be used in combination with other treatments. Xylitol or other non-ionic osmolytes might be included as excipients in the formulation of other pharmaceuticals. Because the activity of many conventional antibiotics is increased at low ionic strength, xylitol (or other low permeability, non-ionic osmolyte) might also be used in the formulation of antibiotics delivered topically, such as tobramycin. For example, xylitol might be used in the formulation of antibiotics delivered as aerosols to airways, delivered as solutions to the external eye, the mouth, the pharynx, and the vagina. In such applications, xylitol could yield additive or synergistic effects of the activity of pharmaceutical antibiotics with the endogenous antimicrobials.

Other applications for the present invention will be also apparent to one of skill in the art. For example, since vaccination and specific treatment for biological warfare are currently inadequate, an alternative to vaccines to protect large populations may be to enhance the activity of the innate immune system. Lowering the ionic strength on the respiratory surface, or other surfaces containing endogenous antimicrobials, may enhance the innate immune system.

Testing of xylitol is shown below in the Examples and the following conclusions can be drawn. The data indicate the xylitol did not have antimicrobial activity on its own, yet when administered to the surface of the nasal epithelium, it decreased the number of coagulase-negative Staphylococcus. These data, plus the finding that xylitol lowered the ASL $Cl^-$ concentration in vitro suggest that the number of nasal bacteria decreased because endogenous antimicrobial factors became more active. However, a lower salt concentration in vivo has not been measured. At the present time, such measurements are problematic (Zabner, J., J. J. Smith, P. H. Karp, J. H. Widdicombe and M. J. Welsh. 1998. Loss of CFTR chloride channels alters salt absorption by cystic fibrosis airway epithelia in vitro. *Mol. Cell.* 2:397–403; Erjef ält, I., and G. G. A. Persson. 1990. On the use of absorbing discs to sample mucosal surface liquids. *Clin. Exp. All.* 20:193–197). Consequently, it cannot be excluded that the possibility that xylitol reduced the number of bacteria by some other mechanism. Although, it is possible that mucociliary clearance was improved, this is unlikely to be entirely responsible because the saline solution administered as a control had no significant effect.

The findings suggest an explanation for the earlier discoveries that xylitol used in chewing gum, in lozenges, or as syrup reduces the risk of caries and prevents acute otitis media (Edgar, W. M. 1998. The benefits of using sugar-free chewing gum: a proven anti-caries effect. *Dr. Dent J.* 184:29–32; Hujoel, P. P., K. K. Mäkinen. 1999. The optimum time to initiate habitual xylitol gum-chewing for obtaining long-term caries prevention. *J. Den. Res.* 78:797–803; Uhari, M., T. Kontiokari and M. Niemelä. 1998. A novel use of xylitol sugar in preventing acute otitis media. *Pediatrics.* 102:879–884; Spitz, I. M., A. H. Rubenstein, I. Bersohn and K. H. Bassler. 1970. Metabolism of xylitol in healthy subjects and patients with renal disease. Metabolism. 19:24). The mouth and oral pharynx contain endogenous antimicrobial factors (Tenovuo, J., M. Luminkari and T. Soukka. 1991. Salivary lysozyme, lactoferrin and peroxidases: antibacterial effects on cariogenic bacteria and clinical applications in preventive dentistry. *Pro. Finn. Dent. Soc.* 87:197–208; Schenkels, L. C., E. C. Veerman and A. V. Nieuw Amerongen. 1995. Biochemical composition of human saliva in relation to other mucosal fluids. *Crit. Rev. Oral. Biol. Med.* 6:161–175). If xylitol administration lowers the salt concentration, the activity of those factors might increase. In the case of acute otitis media, a small decrease in the total number of bacteria at the opening of the Eustachian tube might decrease the frequency of middle ear seeding and infection.

EXAMPLES

Methods

Human Airway Epithelial Model

Airway epithelial cells were isolated from tracheal and bronchial tissue. Cells were seeded onto collagen-coated, semi-permeable membranes (0.6 $cm^2$ Millicel-HA; Millipore, Bedford, Mass.) and grown at the air-liquid interface as previously described (Smith, J. J., S. M. Travis, E. P. Greenberg, and M. J. Welsh. 1996. Cystic fibrosis airway epithelia fail to kill bacteria because of abnormal airway surface fluid. *Cell.* 85:229–236; and erratum 287 (222); Yamaya, M., W. E. Finbeiner, S. Y. Chun, and J. H. Widdicombe. 1992. Differentiated structure and function of cultures from human tracheal epithelium. *Am. J. Physiol.* 262:L713–L724; Zabner, J., B. G. Zeiher, E. Friedman, and M. J. Welsh. 1996. Adenovirus-mediated gene transfer to ciliated airway epithelia requires prolonged incubation time. *J. Virol.* 70:6994–7003). Culture medium, a 1:1 mixture of Dulbecco's modified Eagle's medium and Ham's F12 medium (DME/F12), was supplemented with 2% Ultroser G (BioSepra; Villeneuve, La Garenne, France), and initially with 100 mU/ml penicillin, 100 μg/ml streptomycin, 50 μg/ml streptomycin, 50 μg/ml gentamicin, 25 μg/ml colimycin, 75 μg/ml ceftazidime, 25 μg/ml imipenem, 25 μg/ml cilastinin, and 2 μg/ml fluconazole. Basolateral culture medium was changed every 2–4 days. All epithelia were studied at least 14 days after seeding when they had differentiated. All epithelia were evaluated with scanning electron microscopy for the development of a ciliated apical surface.

For measurement of transepithelial electrical properties, a few epithelia from each culture preparation were mounted in Ussing chambers and studied as previously described (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). Transepithelial resistance was 588±33 Ω·cm$^2$ (n=9) for non-CF and 493±24 Ω·cm$^2$ (n=9) for CF epithelia. The decrease in current after apical addition of 10 μM amiloride was 26.9±1.0 μA·cm$^{-2}$·hr$^{-1}$ (n=9) for non-CF epithelia and 20.0±1.3 μA·cm$^{-2}$·hr$^{-1}$ (n=9) for CF epithelia.

Measurement of Xylitol

Proton nuclear magnetic resonance spectroscopy was used to measure the xylitol concentration in the fluid on the apical surface. For each sample, a 30 μl aliquot of fluid from the apical surface was placed in an NMR tube (Wilmad model 535 pp), then diluted with 600 μl of D$_2$O (Isotec "100%"). Spectra were collected on the Varian INOVA-500 500 MHz spectrometer. In each spectrum, 64 transients were averaged with both the relaxation delay and the acquisition time set to 5 seconds. The spectral width was set to 6000 Hz. 90° pulses of 6.9 μsec were used, and the water signal was suppressed by presaturation at very low power for the entire relaxation delay. Spectra were processed by zero filling the time-domain data to 64 k complex points and apodization with a 0.2 Hz Lorentian line broadening propr to Fourier transformation. All spectra were baseline corrected using a spline function prior to measuring peak integrals. Concentrations were then determined by comparing the measured peak integral to a standard curve for xylitol.

Measurement of Liquid Absorption and Xylitol

Liquid absorption was measured using methods similar to those previously described (Smith, J. J., P. H. Karp, and M. J. Welsh. 1994. Defective fluid transport by cystic fibrosis airway epithelia. *J. Clin. Invest.* 93:1307–1311). To the apical surface, 60 μl of a saline solution, a xylitol solution, or a mixture of the two was applied. The saline solution contained (in mM): 138 NaCl, 4 KCl, 29 NaHCO$_3$, 1.2 CaCl$_2$, 0.6 MgCl$_2$ and 1 NaH$_2$PO$_4$. The xylitol solution contained (in mM): 244 xylitol, 4 KCl, 29 NaHCO$_3$, 1.2 CaCl$_2$, 0.6 MgCl$_2$, 1 NaH$_2$PO$_4$. The osmolality of the submucosal solution was adjusted to equal that of the mucosal solution using a vapor pressure osmometer (Wescor Inc., Logan, Utah). After incubation for 4 hours, apical solutions were collected under mineral oil and their volume measured as previously described (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403; Smith, J. J., P. H. Karp, and M. J. Welsh. 1994. Defective fluid transport by cystic fibrosis airway epithelia. *J. Clin. Invest.* 93:1307–1311).

Measurement of ASL Cl$^-$ Concentration

The ASL Cl$^-$ concentration was measured as previously described (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). To the apical surface of epithelia, 5 μl of a saline solution or a xylitol solution was applied. The xylitol solution contained (in mM): 290 xylitol, 1.2 CaCl$_2$, and 0.6 MgCl$_2$. The saline solution contained (in mM): 145 NaCl, 1.2 CaCl$_2$, and 0.6 MgCl$_2$. The basolateral medium (500 μl) of epithelia was spiked with 2.5×10$^4$ cpm of $^3$H$_2$O and $^{36}$Cl, and then placed in a sealed chamber containing a water-saturated atmosphere of 5% CO$_2$ in air. Water used for chamber humidification was labeled with the same specific activity of $^3$H$_2$O to ensure that at equilibrium the ratio of labeled to unlabeled water would be identical in the water vapor, culture medium, and ASL. Non-CF and CF epithelia were always studied at the same time in the same chamber. Earlier studies indicated that there were no interventions on the apical surface, the tracer content of ASL had reached equilibrium by 24 hours (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). After incubation at 37° C. for 24 hours, ASL was collected by rapidly rinsing the apical surface with 100 μl of medium. The ratio of $^{36}$Cl to $^3$H$_2$O was determined by liquid scintillation. Aliquots of submucosal solution were also collected for measurement of $^{36}$Cl and $^3$H$_2$O and for measurement of Cl$^-$ concentration by flame photometry. From these measurements, it was determined the $^3$H$_2$O activity per μl of water and the cpm of $^{36}$Cl per mole of Cl$^-$ in the basolateral medium. ASL volume was calculated from the ASL $^3$H$_2$O collected divided by the ratio of $^3$H$_2$O activity per μl of basolateral medium. Chloride content was calculated from the ASL $^{36}$Cl collected divided by the ratio of $^{36}$Cl per mole of Cl$^-$ in the basolateral medium ASL Cl$^-$ concentration was calculated from the Cl$^-$ content divided by the volume of ASL.

Evaluation of the Effect of Xylitol on Bacterial Growth

Nasal lavage fluid was collected from normal volunteers. A flexible catheter (18-gauge; Jelco, Tampa, Fla.) was inserted into each nostril and the area flushed four times with 4 ml of sterile water. Cells were removed by centrifugation and the fluid was filtered with a sequential 0.8/0.2 μm Supor Acrodisc PF (GelamnSciences, Ann Arbor, Mich.). To study the effect of xylitol on bacterial killing by endogenous antimicrobial factors, a luminescence assay was used in which *E. coli* express the genes from *Photorhabdus luminescens* (Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell. Mol. Biol.* 20:872–879). As previously described, this assay reports bacterial viability. Briefly, bacteria were grown to exponential phase at 30° C., centrifuged, and resuspended in 20 mM potassium phosphate with 2% Lauria-Bertani medium. Bacteria (10$^6$) were incubated with 50 μl of nasal lavage fluid into serial dilutions of 300 mM xylitol or 150 mM NaCl in a 96 well plate. After incubation at 30° C. for 4 hours, luminescence was measured with a luminometer (MLX Luminometer; Dynex Technologies Inc.; Chantilly, Va.). The relative light units were used to determine percent bacterial killing.

To test the effect of xylitol on growth of different airway pathogens in a carbon-starved media, *P. aeruginosa*, *S. aureus*, and coagulase-negative Staphylococcus were grown overnight in Lauria-Bertani medium. The bacteria were then centrifuged and resuspended in M9 media containing either 100 mM succinate, mannitol, or sucrose, respectively, and grown overnight at 37° C. The bacteria were centrifuged and resuspended in M9 media alone. M9 media containing 100 mM xylitol, or 100 mM of the indicated metabolizable sugar, as positive control. The optical density (O.D.) was measured after 0, 1, 2, and 4 hours at 600 nm on a Beckman DU640 Spectrophotometer (Schaumburg, Ill.). To test the antibiotic effect of xylitol, *P. aeruginosa, S. aureus*, and coagulase-negative Staphylococcus were grown overnight in Lauria-Bertani medium. The bacteria were then centrifuged and resuspended in Lauria-Bertani media with and without 100 mM xylitol. As a positive control, antibiotics with specific activity to each of the bacteria were added to the media (40 $\mu$g/ml tobramycin or 40 $\mu$g/ml levofloxacin).

To test the effect of xylitol on growth of normal nasal flora in a carbon-starved media, nasal swabs were obtained from 3 normal volunteers and the swabs were inoculated into M9 media alone, M9 with 100 mM xylitol, or Lauria-Bertani media. The media were incubated at 37° C. for 72 hours and the O.D. were recorded.

Administration of Xylitol to the Nasal Mucosa

Subjects were over 18 years old. Individuals were excluded from participation if they had a seasonal allergic rhinitis or nasal polyps, or current treatment with any antibiotic, steroid, or topical intranasal preparation. Twenty-one normal healthy subjects (10 male and 11 female, age 20 to 52 years) participated.

The design was a double-blind, randomized, cross-over study. Subjects were randomized to one of two groups: xylitol followed by saline or saline followed by xylitol. A culture of both anterior nares was obtained on day zero. Then subjects sprayed each nostril with a prefilled syringe of solution 4 times per day for 4 days. On the morning of day 5, subjects did their final application at breakfast time, then a nasal swab was obtained 2 hours later. No treatment was administered for the next 7 days. Subjects then repeated the protocol with the opposite solution. The saline solution was 0.9% NaCl in water (Baxter Health Care Corp., Deerfield, Ill.). The xylitol solution was 5% xylitol (304 mM) in water. The solutions were nebulized using an Accuspray syringe (Becton Dickinson Pharmaceutical Systems, Franklin Lakes, N.J.), containing 250 $\mu$l of solution. The xylitol and saline syringes were identical. The mass medium diameter of particles was ~60 $\mu$m. It was impossible to disguise the sweet taste of xylitol. Fifteen of the 21 subjects were able to recognize the sweet taste of xylitol; the other 6 subjects could not distinguish between the solutions.

Samples for cultures were obtained with sterile rayon swabs (Culturette Collection and Transport System, Becton Dickinson Microbiology Systems, Sparks, Md.). A swab was rotated firmly 5 times in each nostril. Nasal swabs on each subject were performed by the same individual for the entire study. Each swab was directly inoculated onto 1 ml of PBS and vortexed for 5 seconds. The 50 $\mu$l of the bacteria solution were then plated using an automated spiral plater (Spiral Biotech, Bethesda, Md.) onto sheep blood agar plates (Remel, Lenexa, Kans.), and mannitol salt agar (Becton Dickenson, Sparks, Md.). The plates were incubated at 37° C. for 24 hours and the colonies of coagulase-negative Staphylococcus colonies were identified and counted using a Cling-On Grid (Spiral Biotech, Bethesda, Md.). Samples were sent to the microbiology laboratory to confirm the identity of the bacteria.

In a preliminary study in 8 subjects, it was found the number of coagulase-negative Staphylococcus cultured from the nasal epithelium remained relatively stable over 4 days. A power analysis (1988. Statistical power analysis for the behavioral sciences. Lawrence Erlbaum Associates Inc., Hillsdale, N.J.) suggested that 39 independent nostrils would be required to show a 50% difference in the reduction of coagulase-negative Staphylococcus between the treatments (power of 0.84 and an f value of 0.5 and assuming that the nostrils are independent).

Example 1

Xylitol Permeability of Airway Epithelia

Figure 1A:
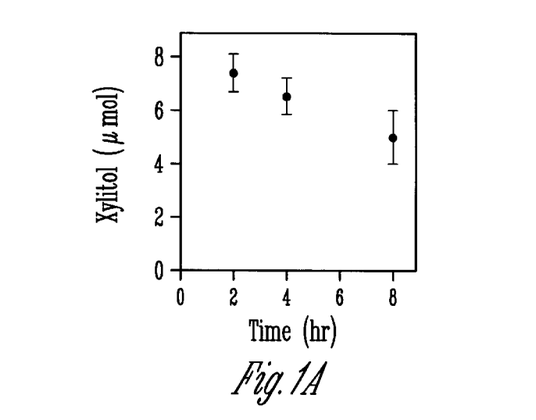
Figure 1B:
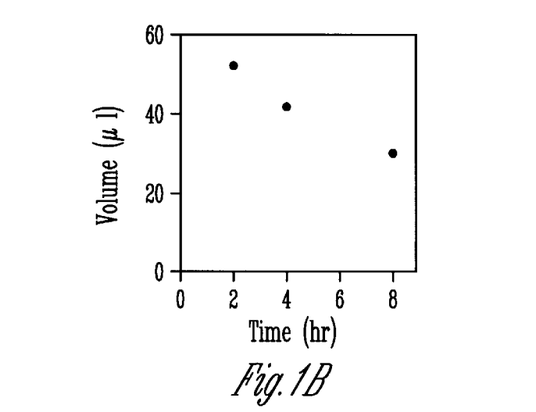
Figure 1C:
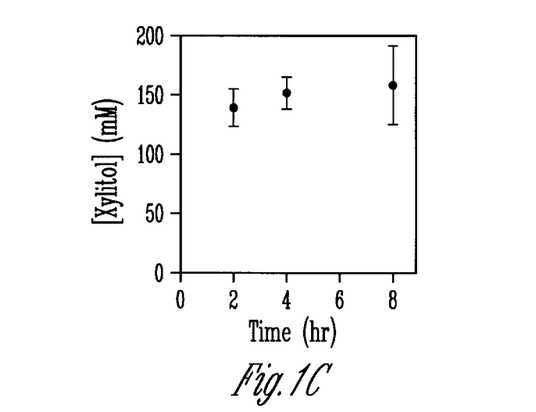

Primary cultures of non-CF and CF airway epithelia were used to examine the effect of xylitol on ASL. When grown at the air-liquid interface for 10–14 days, the epithelia differentiate, develop ciliated apical surfaces, and assume the electrolyte transport properties of native epithelium (Yamaya, M., W. E. Finbeiner, S. Y. Chun, and J. H. Widdicombe. 1992. Differentiated structure and function of cultures from human tracheal epithelium. *Am. J. Physiol.* 262:L713–L724; Zabner, J., B. G. Zeiher, E. Friedman, and M. J. Welsh. 1996. Adenovirus-mediated gene transfer to ciliated airway epithelia requires prolonged incubation time. *J. Virol.* 70:6994–7003). Because airway epithelia are water permeable (Folkesson, H. G., M. A. Matthay, A. Frigeri, and A. S. Verkman. 1996. Transepithelial water permeability in microperfused distal airways. *J. Clin. Invest.* 97:664–671), lowering ASL salt concentration requires an osmolyte with a relatively low transepithelial permeability. Xylitol permeability was tested by applying it to the apical surface and measuring its disappearance over time. With time, the amount of xylitol decreased (FIG. 1); after 11 hours, approximately half the applied sugar would diffuse to the basolateral surface. Because the volume decreased, the xylitol concentration increased. Thus, the xylitol permeability was not high and the increase in concentration suggested that xylitol could temporarily hold liquid on the apical surface.

Figure 2:
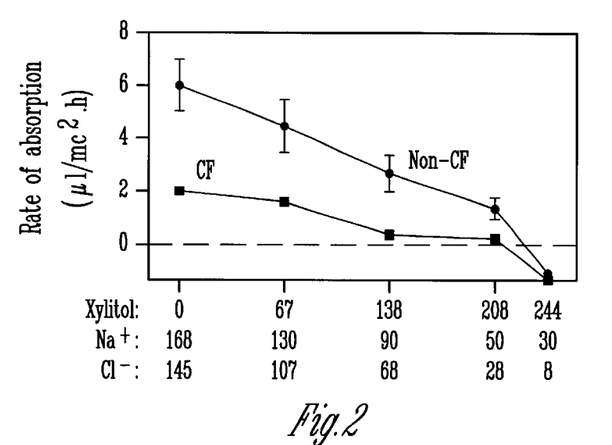

To test this directly, it was examined whether xylitol reduces the rate of liquid absorption. Sixty $\mu$l of a saline solution, a xylitol solution or a mixture of the two was applied to the apical surface. The apical solution always has the same osmolarity as the basolateral solution; thus, as the xylitol concentration increased, the NaCl concentration decreased. Four hours later, the liquid was removed and the rate of liquid absorption determined. FIG. 2 shows that during 4 hours with apical saline both non-CF and CF epithelia absorbed liquid, consistent with previous reports (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403; Matsui, H., B. R. Grubb, R. Tarran, S. H. Randell, J. T. Gatzy, C. W. Davis, and R. C Boucher. 1998. Evidence for periciliary liquid layer depletion, not abnormal ion composition, in the pathogenesis of cystic fibrosis airways disease. *Cell.* 95:1005–1015; Smith, J. J., P. H. Karp, and M. J. Welsh. 1994. Defective fluid transport by cystic fibrosis airway epithelia. *J. Clin. Invest.* 93:1307–1311; Jiang, C., W. E. Finkbeiner, J. H. Widdicombe, P. B. J. McCray, and S. S. Miller. 1993. Altered fluid transport across airway epithelium in cystic fibrosis. *Science.* 262:424–427). Moreover, the rate of liquid absorption was greater in non-CF than CF epithelia (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). In both non-CF and CF epithelia, increasing the xylitol concentration reduced the rate of liquid absorption (FIG. 2). These data indicate that xylitol is relatively non-permeable because it reduced the absorption rate and held liquid on the apical surface.

Example 2

Figure 3A:
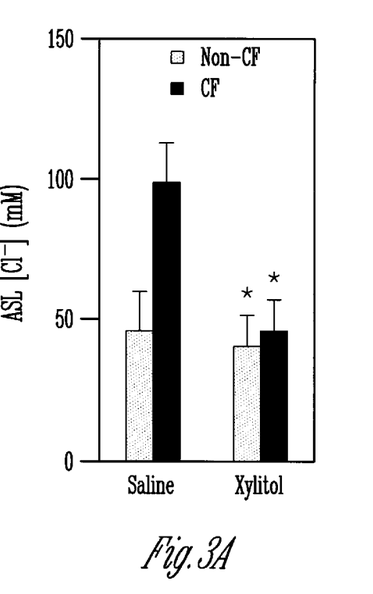

Xylitol Added to the Apical Surface Decreases ASL Cl⁻ Concentration in CF Epithelia in Vitro Xylitoll's ability to dilute the ASL salt concentration was tested by applying a small volume (5 μl) of saline or xylitol to the apical surface. Twenty-four hours after applying the saline (138 mM Cl⁻) non-CF epithelia reduced the ASL Cl⁻ concentration to 45.3±1.3 mM (FIG. 3A). This value agrees with earlier measurements of ASL Cl⁻ concentration (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). When xylitol was applied instead of saline, the ASL Cl⁻ concentration was even lower (34.2±4.3 mM).

Figure 3B:
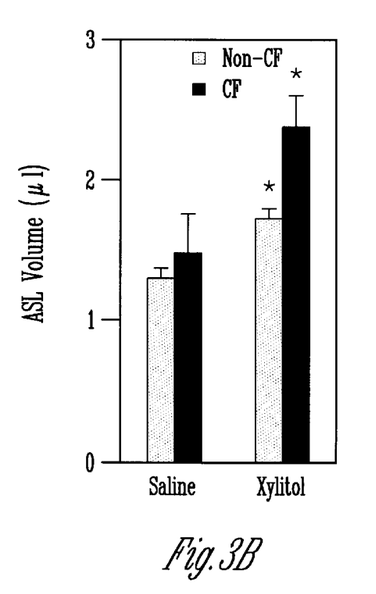

In CF epithelia, the Cl⁻ concentration was 98±12 mM 24 hours after saline addition (FIG. 3A). This value is approximately double that in non-CF epithelia, and is consistent with earlier measurements (Zabner, J., J. J. Smith, P. H. Karp, J. H. Widdicombe, and M. J. Welsh. 1998. Loss of CFTR chloride channels alters salt absorption by cystic fibrosis airway epithelia in vitro. *Mol. Cell.* 2:397–403). However, with xylitol application, the Cl⁻ concentration fell to values observed in non-CF epithelia. Xylitol also increased the estimated ASL volume in both non-CF and CF epithelia (FIG. 3B). Thus, adding xylitol to the CF epithelial surface allowed a reduction in Cl⁻ concentration likely due to a combination of active transepithelial salt transport, ASL dilution, and the osmotic pressure generated by xylitol.

Example 3

Figure 4:
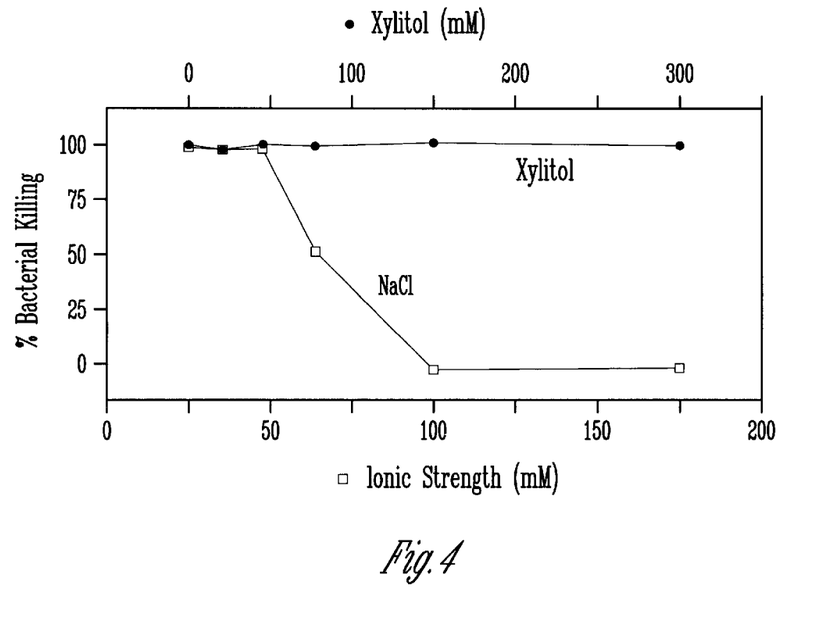
FIG. 4. Effect of modifying ionic strength and xylitol concentration of killing of *E. coli* by nasal lavage liquid. Nasal lavage liquid was diluted with increasing concentrations of NaCl (bottom X-axis) or xylitol (top X-axis). SEM are smaller than the symbol.

Xylitol does not Affect Bacterial Growth and does not Interfere with Killing by Endogenous Antimicrobial Factors Earlier data indicated that an increase in osmolarity did not inhibit bacterial killing by endogenous airway antimicrobial factors; rather it was increased ionic strength that inhibited killing (Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am.J. Respir. Cell Mol. Biol.* 20:872–879). To test the effect of xylitol, nasal lavage fluid was collected, which contains multiple antimicrobial factors and killing of *E. coli* was examined using a luminescence assay (Travis, S. M., B. A. D. Conway, J. Zabner, J. J. Smith, N. N. Anderson, P. K. Singh, E. P. Greenberg, and M. J. Welsh. 1999. Activity of Abundant Antimicrobials of the Human Airway. *Am. J. Respir. Cell Mol. Biol.* 20:872–879). FIG. 4 shows that nasal lavage fluid killed *E. coli*. Although killing was inhibited as ionic strength increased, killing was not affected by an increase in xylitol concentration. Similar results were obtained with *P. aeruginosa* and *S. aureus*.

Figure 5A:
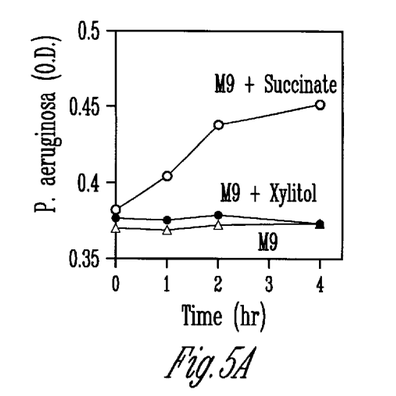
Figure 5B:
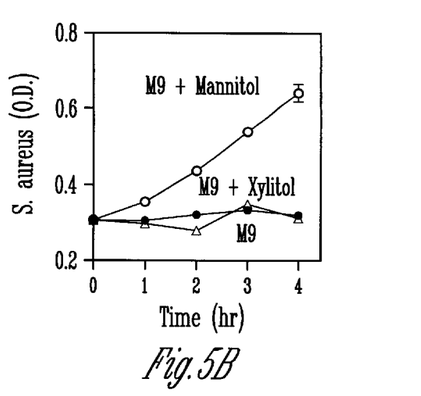
Figure 5C:
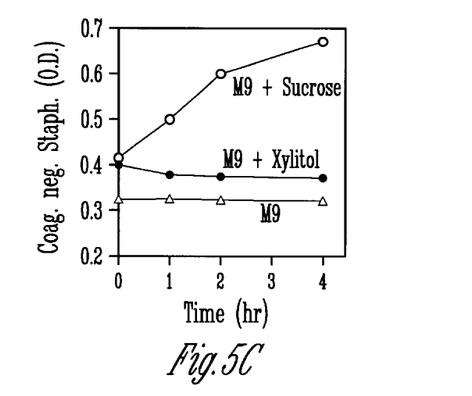
Figure 5D:
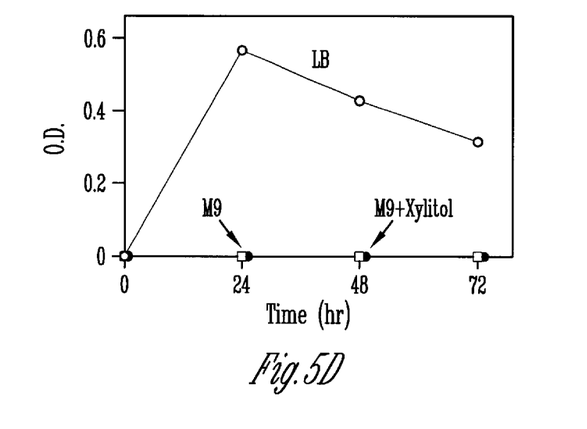

It was tested whether xylitol would support bacterial growth. *P. aeruginosa* were placed in M9 media, which lacks a carbon source. Under these conditions, the bacteria showed no growth (FIG. 5A). Adding the metabolizable sugar succinate allowed bacterial growth. In contrast, there was no growth of *P. aeruginosa* when M9 media was supplemented with xylitol. Likewise, xylitol failed to support growth of *S. aureus* or coagulase-negative Staphylococcus (FIGS. 5B and 5C). To determine whether bacteria from the nasal surface could utilize xylitol for growth, nasal swabs were obtained and inoculated into media. In Lauria-Bertani media bacteria grew, whereas in M9 media alone, or M9 media containing xylitol, there was no growth (FIG. 5D).

Figure 5E:
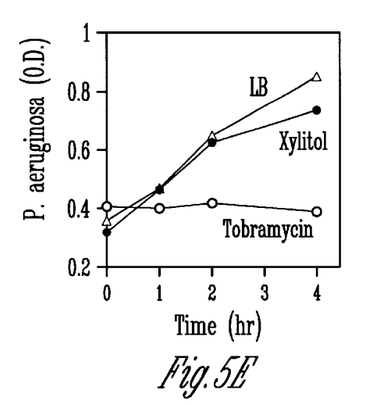
Figure 5F:
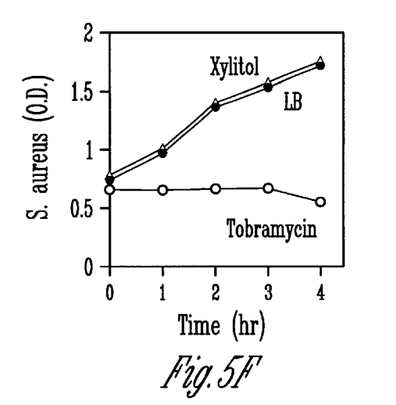
Figure 5G:
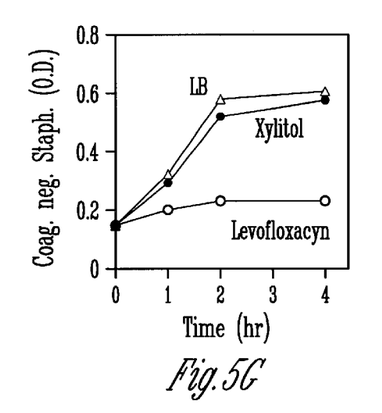

Although xylitol did not support growth, it had no antibacterial activity on its own. FIGS. 5E–5G show that xylitol did not inhibit the growth of *P. aeruginosa, S. aureus*, or coagulase-negative Staphylococcus in rich media As a positive control, a pharmaceutical antibiotic to which the bacteria were sensitive was added.

The results indicate that xylitol is relatively inert in terms of CF pathogens and bacteria on the nasal surface: it does not inhibit the effect of endogenous antibiotics; it does not serve as a ready carbon source for growth; and it does not have antibiotic effects of its own.

Example 4

Xylitol Applied to Nasal Epithelia in Vivo Reduces the Number of Coagulase-negative Staphylococcus The ability of xylitol to lower ASL Cl⁻ concentration in vitro and its relatively inert behavior toward bacteria, suggested the hypothesis that xylitol might lower ASL salt concentration in patients with CF, thereby enhancing bacterial killing by endogenous antimicrobial factors. However, this is difficult to test for two reasons. First, as indicated above, methods to accurately measure ASL salt concentration in vivo remain problematic. Second, as discussed below, testing the efficacy of any agent to prevent or delay the onset of pulmonary infections in CF would require a large clinical study in infants. Therefore, a simpler approach was sought, which although not testing the hypothesis directly, provides proof of concept. The effect of xylitol administration of bacteria cultured from the nasal mucosa of non-CF individuals was examined. The bacteria can be obtained readily with a swab and are easily counted.

Normal subjects were chosen for this study because in preliminary experiments it was found that the number of bacteria cultured from the CF nasal surface are quite variable. Moreover, most CF patients are using either systemic or inhaled antibiotics, introducing a confounding variable. Because *P. aeruginosa* is rare and *S. aureus* is not common on normal mucosa, the number of coagulase-negative Staphylococcus were counted, an organism commonly found on the nasal mucosa (Citron, D. M., M. A. C. Edelstein, L. S. Garcia, G. D. Roberts, R. B. Thomson, and J. A. Washington. 1994. Microorganisms encountered in the respiratory tract. In Bailey & Scott's Diagnostic Microbiology. E. J. Baron, L. R. Peterson, and S. M. Finegold, editors. Mosby, St. Louis. 219–233; Woods, G. L., and J. A. Washington. 1995. The clinician and the microbiology laboratory. In Principles and Practice of Infectious Diseases. G. L. Mandell, J. E. Bennett, and R. Dolin, editors. Churchill Livingstone, N.Y. 169–175) and one that is related to *S. aureus*.

A randomized, double-blind, cross-over study was performed. The nasal mucosa was swabbed and the number of coagulase-negative Staphylococcus was determined by culture. Subjects then administered xylitol or a NaCl solution to both nostrils 4 times a day. After 4 days, the number of nasal coagulase-negative Staphylococcus was counted again. Following a 1 week recovery period, the nasal swabs to measure number of bacteria and the 4 day treatment period were repeated with the other treatment. The intervention (290 mM xylitol or 145 mM saline) for the first treatment was chosen at random. These agents were applied to both nostrils in 250 μl using a pre-loaded syringe spray device. Twenty-one subjects participated.

Figure 6:
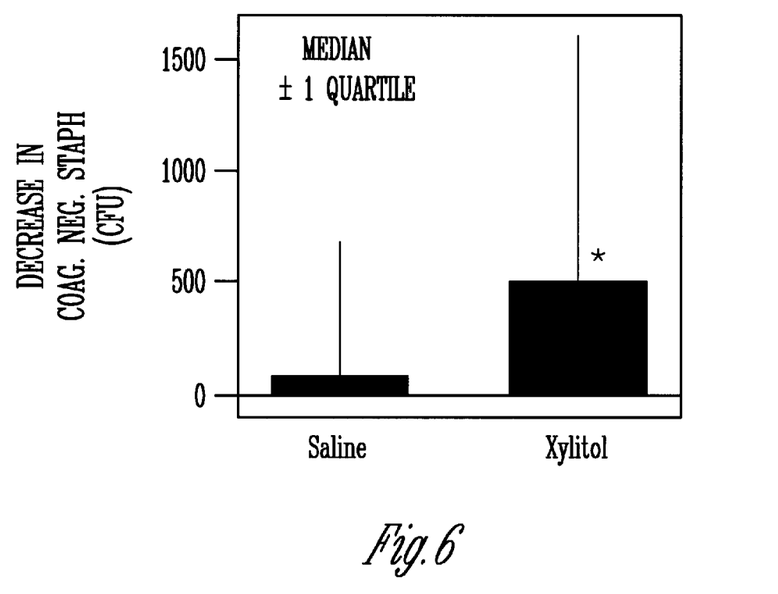
FIG. 6. Effect of xylitol administration to nasal mucosa on coagulase-negative Staphylococcus. Data are decreased in cfu of coagulase-negative Staphylococcus after treatment with either saline or xylitol. Shown are median± one quartile. Asterisk indicates p=0.05.

FIG. 6 shows the median change in bacterial numbers following xylitol or saline administration. Analysis of variance for a cross-over design was applied on the change in bacterial count from pretreatment to post treatment. The factors included in the ANOVA model were treatment, sequence of treatment, and nostril side. Prior to the analysis, a square root transformation (sign of change times square root change) was used to normalize the data. The analysis showed that there were no significant effect of the sequence or the nostril. Thus, the comparison of xylitol vs. saline was evaluated from the data of both nostrils and both sequences. The average reduction in the xylitol treated nostrils was 597±242 cfu compared to saline at 99.3±104, p=0.05. The median change was 500 (interquartile range of 1152 to 120) for xylitol and for saline 89 (interquartile range of 540 to −53)(FIG. 6). Xylitol significantly reduced the number of coagulase-negative Staphylococcus on the nasal surface compared to saline.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for killing infectious microbial cells comprising
    exposing said infectious microbial cells to endogenous antimicrobials in bodily fluids by contacting body surfaces which secrete these bodily fluids with an effective amount of non-ionic osmolytes to a layer of liquid covering an airway surface so that said killing is able to occur in the absence of absorption of the non-ionic osmolyte, and further reducing the active transepithelial salt transport on said layer of liquid covering the airway surface, and promoting said endogenous antimicrobials killing of said infectious microbial cells.

2. The method of claim 1 wherein ionic strength of the bodily fluid is lowered thereby enhancing the innate immunity.

3. The method of claim 1 wherein the non-ionic osmolyte on a layer of liquid covering the airway surface is xylitol.

4. A method for killing infectious microbial cells comprising decreasing ionic strength in fluid containing endogenous antimicrobials by applying an effective amount of non-ionic osmolyte to a layer of liquid covering an airway surface so that a killing is able to occur in the absence of absorption of the non-ionic osmolyte, and further reducing the active transepithelial salt transport on said layer of liquid covering the airway surface, and promoting an endogenous antimicrobials killing of said infectious microbial cells.

5. A method of treating respiratory tract infections associated with cystic fibrosis comprising administering to a patient having cystic fibrosis an effective amount of a non-ionic osmolyte to a layer of liquid covering an airway surface so that a treating is able to occur in the absence of absorption of the non-ionic osmolyte, and further reducing the active transepithelial salt transport on said layer of liquid covering the airway surface.

6. The method of claim 5 wherein the non-ionic osmolyte on a layer of liquid covering the airway surface is xylitol.

7. The method of claim 5 wherein the effective amount lowers the ionic strength of said layer of liquid covering the airway surface.

8. The method of claim 5 wherein the osmolyte is administered via an aerosol.

9. The method of claim 5 wherein the osmolyte is administered via a powder.

10. A method of preventing respiratory infections in a patient in need thereof, comprising administering to the patient an effective amount of a non-ionic osmolyte to a layer of liquid covering an airway surface so that a killing is able to occur in the absence of absorption of the non-ionic osmolyte, and further reducing the active transepithelial salt transport on said layer of liquid covering the airway surface.

11. The method of claim 10 wherein the osmolyte is administered via an aerosol.

12. The method of claim 10 wherein the osmolyte is administered via a powder.

13. The method of claim 10 wherein the osmolyte is xylitol.

14. The method of claim 10 wherein the effective amount lowers the ionic strength of said layer of liquid covering the airway surface.

15. A method of preventing airway infection comprising administering an amount of a non-ionic osmolyte to a layer of liquid covering an airway surface so that said prevention of infection is able to occur in the absence of absorption of the non-ionic osmolyte, and further reducing the active transepithelial salt transport on said layer of liquid covering the airway surface, wherein the osmolyte lowers the ionic strength of the surface liquid wherein the surface liquid contains endogenous antimicrobials.

16. The method of claim 15 wherein said non-ionic osmolyte on a layer of liquid covering the airway surface is xylitol.

* * * * *